US007585848B2

(12) United States Patent
Masuda et al.

(10) Patent No.: US 7,585,848 B2
(45) Date of Patent: Sep. 8, 2009

(54) METHODS AND COMPOSITIONS FOR TREATING, INHIBITING AND REVERSING DISORDERS OF THE INTERVERTEBRAL DISC

(75) Inventors: Koichi Masuda, Wilmette, IL (US); Takefumi Gemba, Kawanishi (JP)

(73) Assignees: Rush University Medical Center, Chicago, IL (US); Anges MG, Inc., Osaka (JP)

( * ) Notice: Subject to any disclaimer, the term of this patent is extended or adjusted under 35 U.S.C. 154(b) by 391 days.

(21) Appl. No.: 11/033,466

(22) Filed: Jan. 11, 2005

(65) Prior Publication Data

US 2006/0153847 A1    Jul. 13, 2006

(51) Int. Cl.
*A61K 31/70* (2006.01)
*C07H 21/04* (2006.01)

(52) U.S. Cl. ............... 514/44; 536/23.1; 536/24.5

(58) Field of Classification Search .............. None
See application file for complete search history.

(56) References Cited

U.S. PATENT DOCUMENTS

| | | | |
|---|---|---|---|
| 5,591,840 | A | 1/1997 | Narayanan et al. |
| 6,262,033 | B1 | 7/2001 | Morishita et al. |
| 6,399,376 | B1 | 6/2002 | Melford et al. |
| 6,410,516 | B1 | 6/2002 | Baltimore et al. |
| 2001/0006948 | A1 | 7/2001 | Kang |
| 2003/0113796 | A1* | 6/2003 | Sims .................... 435/7.1 |
| 2004/0072726 | A1 | 4/2004 | Morshita et al. |
| 2006/0241066 | A1 | 10/2006 | Tomita et al. |

FOREIGN PATENT DOCUMENTS

| | | |
|---|---|---|
| CA | 2102704 | 11/1992 |
| CA | 2131587 | 3/1995 |
| EP | 0589330 | 3/1994 |
| EP | 0 824 918 A1 * | 2/1998 |
| EP | 0824918 | 2/1998 |
| EP | 1512415 | 3/2005 |
| JP | 6-209778 | 9/1993 |
| JP | 06/508029 | 9/1994 |
| JP | 07/170998 | 7/1995 |
| WO | WO 95/11687 | 5/1995 |
| WO | WO 95/12415 | 5/1995 |
| WO | WO 03/099339 | 4/2003 |

OTHER PUBLICATIONS

Levicoff et al (Gene Therapy for disc repai. The Spine Journal, 2005. 5:287S-296S).*
Singh et al (Animal Models for human disc degeneration, The Spine Journal, 2005. 5:267S-279S).*
Tomita et al (Transcription Factors as Molecular Targets: Molecular Mechanisms of Decoy ODN and their Design. Current Drug Targets, 2003. 4:603-608).*
Bielinska et al. "Regulation of Gene Expression with Double-Stranded Phosorothioate Oligonucleotides." *Science*, Nov. 16, 1990, vol. 250: 997-1000.
Neish et al. "Functional Analysis of the Human Vascular Cell Adhesion Molecule 1 Promoter." *J. Exp. Med.*, Dec. 1992, vol. 176: 1583-1593.
Narayanan et al. "Evidence for Differential Functions of the p50 and p65 Subunits of NF-κB with a Cell Adhesion Model." *Molecular and Cellular Biology*, Jun. 1993: 3802-3810.
Sokoloski et al. "Antisense Oligonucleotides to the p65 Subunit of NF-κB Block CD11b Expression and Alter Adhesion Properties of Differentiated HL-60 Granulocytes." *Blood*, Jul. 15, 1993, vol. 82, No. 2: 625-632.
Eck et al. "Inhibition of Phorbol Ester-Induced Cellular Adhesion by Competitive Binding of NF-κB in Vivo." *Molecular and Cellular Biology*, Oct. 1993: 6530-6536.
Higgins et al. "Antisense inhibition of the p65 subunit of NF-κB blocks tumorigenicity and causes tumor regression." *Proc. Natl. Acad. Sci. USA*, Nov. 1993, vol. 90: 9901-9905.
Kaltschmidt et al. "Transcription factor NF-κB is activated in microglia during experimental autoimmune encephalomyelitis." *Journal of Neuroimmunology*, vol. 55 (1994): 99-106.
Nakajima et al. "Involvement of NF-κB Activation in Thrombin-Induced Human Vascular Smooth Muscle Cell Proliferation." *Biochemical and Biophysical Research Communications*, Oct. 1994, vol. 204, No. 2: 950-955.
Kang, et al. "Herniated Lumbar Intervertebral Discs Spontaneously Produce Matrix Metalloproteinases, Nitric Oxide, Interleukin-6, and Prostaglandin $E_2$." *Spine*, Feb. 1, 1996, vol. 21, No. 3: 271-277.
Morishita et al. "Role of Transcriptional cis-Elements, Angiotensinogen Gene-Activating Elements, of Angiotensinogen Gene in Blood Pressure Regulation." *Hypertension*, vol. 27(1996): 502-507.
Tomita et al. "A Novel Strategy for Gene Therapy and Gene Regulation Analysis Using Transcription Factor Decoy Oligonucleotides." *Experimental Nephrology* (1997): 5:429-434.
Barnes, Peter J. "Molecules in Focus: Nuclear Factor-κB." *Int. J. Biochem. Cell. Biol.*, vol. 29, No. 6(1997): 867-870.
Morishita et al. "In Vivo Transfection of Cis Element 'Decoy' Against Nuclear Factor-κB Binding Site Prevents Myocardial Infarction." *Nature Medicine*, Aug. 1997, vol. 3, No. 8: 894-899.
Sawa et al. "A Novel Strategy For Myocardial Protection Using in Vivo Transfection of *cis* Element 'Decoy' Against NFκB Binding Site." *Circulation*, Nov. 1997, vol. 96(9): 11-281—11-285.
Morishita et al. "Application of Transcription Factor 'Decoy' Strategy As Means of Gene Therapy and Study of Gene Expression Cardiovascular Disease." *Cir. Res.*, vol. 82(1998): 1023-1028.
Morishita et al. "Oligonucleotide-Based Gene Therapy for Cardiovascular Disease." *Clin Chem Lab Med.*, vol. 36(8)(1998): 529-534.

(Continued)

*Primary Examiner*—Richard Schnizer
(74) *Attorney, Agent, or Firm*—Foley & Lardner LLP

(57) ABSTRACT

Described herein are methods and compositions for inhibiting, treating and reversing intervertebral disc disorders using transcription factor inhibitors. In certain embodiments, the transcription factor inhibitor targets the transcription factor NF-κB. Also described are methods and compositions where intervertebral disc disorder is reversed using a decoy oligodeoxy-nucleotide that blocks NF-κB.

9 Claims, 3 Drawing Sheets

OTHER PUBLICATIONS

Ono et al. "Decoy Administration of NF-κB into the Subarachnoid Space For Cerebral Angiopathy." *Human Gene Therapy*, May 1, 1998, 9:1003-1011.

Tomita et al. "Transcription factor decoy for nuclear factor-κB inhibits tumor necrosis factor-α-induced expression of interleukin-6 and intracellular adhesion molecule-1 in endothelial cells," *Journal of Hypertension*, Jul. 1998, vol. 16:993-1000.

Epinat et al. "Diverse agents act at multiple levels to inhibit the Rel/NF-κB signal transduction pathway." *Oncogene*, vol. 18 (1999): 6896-6909.

Kawamura et al. "Intratumoral injection of oligonucleotides to the NFκB binding site inhibits cachexia in a mouse tumor model." *Gene Therapy*, Jan. 1999, vol. 6(1): 91-97.

Tomita et al. "Suppressed Severity of Collagen-Induced Arthritis by In Vivo Transfection of Nuclear Factor κB Decoy Oligodeoxynucleotides As A Gene Therapy." *Arthritis & Rheumatism*, Dec. 1999, vol. 42, No. 12: 2532-2542.

Menetski, Joseph P. "The Structure of the Nuclear Factor κ-B Protein-DNA Complex Varies with DNA-binding Site Sequence." *The Journal of Biological Chemistry*, Mar. 17, 2000, vol. 275, No. 11:7619-7625.

Tomita et al. "In Vivo Administration of a Nuclear Transcription Factor-κB Decoy Suppresses Experimental Crescentic Glomerulonephritis," *J. Am. Soc. Nephrol.*, vol. 11 (2000): pp. 1244-1252.

Matsushita et al. "Hypoxia-Induced Endothelial Apoptosis Through Nuclear Factor-κB (NF-κB)-Mediated bcl-2 Suppression: In Vivo Evidence of the Importance of NF-κB in Endothelial Cell Regulation." *Circulation Research*, May 2000, vol. 86(9): 974-81.

Tomita et al. "Transcription factor decoy for NFκB inhibits cytokine and adhesion molecule expressions in synovial cells derived from rheumatoid arthritis." *Rheumatology* (Oxford), Jul. 2000, vol. 39(7): 749-57.

Suzuki et al. "Decoy against nuclear factor-κB attenuates myocardial cell infiltration and arterial neointimal formation in murine cardiac allografts." *Gene Therapy*, Nov. 2000, vol. 7(21): 1847-52.

Tomita et al. "Inhibition of TNF-α, Induced Cytokine and Adhesion Molecule." *Exp. Nephrol.*, vol. 9(3) (2001): 181-90.

Kawamura et al. "Intravenous injection of oligodeoxynucleotides to the NF-κB binding site inhibits hepatic metastasis of M5076 reticulosarcoma in mice." *Gene Therapy*, Jun. 2001, vol. 8(12): 905-12.

Zhao et al. "Adenovirus-mediated TGF-$\beta_1$ gene transfer to human degenerative lumbar intervertebral disc cells." *Chinese Medical Journal*, vol. 115, No. 3(2002): 409-412.

Ahn et al. "Inhibitory Effects of Novel AP-1 Decoy Oligodeoxynucleotides on Vascular Smooth Muscle Cell Proliferation in Vitro and Neointimal Formation in Vivo." *Circulation Research*, 90(2002): 1325-32.

Crinelli et al. "Design and characterization of decoy oligonucleotides containing locked nucleic acids." *Nucleic Acids Research*, vol. 30, No. 11(2002): 2435-43.

Freemont et al. "Current understanding of cellular and molecular events in intervertebral disc degeneration: implications for therapy." *Journal of Pathology*, vol. 196(2002): 374-379.

Vincenti et al. "Transcriptional regulation of collagenase (MMP-1, MMP-13) genes in arthritis: integration of complex signaling pathways for the recruitment of gene-specific transcription factors." *Arthritis Research*, vol. 4(2002): 157-164.

Nakamura et al. "Prevention and regression of atopic dermatitis by ointment containing NF-κB decoy oligodeoxynucleotides in NC/Nga atopic mouse model." *Gene Therapy*, Sep. 2002, vol. 9: 1221-1229.

Morishita et al. "Therapeutic Potential of Oligonucleotide-Based Therapy in Cardiovascular Disease," *Biodrugs*, vol. 17, No. 6(2003): 383-389.

Firestein, Gary S. "NF-κB: Holy Grail for Rheumatoid Arthritis?" *Arthritis & Rheumatism*, Aug. 2004, vol. 50, No. 8: 2381-2386.

Yokoseki et al. "*cis* Element Decoy Against Nuclear Factor-κB Attenuates Development of Experimental Autoimmune Myocarditis in Rats." Circulation Research, Nov. 9, 2001, 89: 899-906.

International Search Report for PCT/US2006/000788 dated Aug. 29, 2007.

Autieri et al., Antisense oligonucleotides to the P65 subunit of NF-κB inhibit human cascular smooth muscle cell adherence and proliferation and prevent neointima formation in rate carotid arteries, *Biochemical and Biophysical Research Communications*, 213(3):827-836 (Aug. 24, 1995).

Kitajima et al., Abiation of transplanted HTLV-I tax-transformed tumors in mice by antisense inhibition of NF-κB, *Science*, 258:1792-1795 (Dec. 11, 1992).

Pinkenburg et al., Inhibition of NF-κB mediated inflammation by siRNA expressed by recombinant adeno-associated virus, *Journal of Virological Methods*, 120:119-122 (2004).

Akeda, K. et al., "P89. The intra-discal injection of naked NFkappaB decoy oligonucleotide is effective in restoring disc degeneration in the rabbit annular needle puncture model," The Spine Journal, Elsevier, vol. 5, No. 4, pp. 152S-153S, Jul. 2005.

Gruber, H. E. et al. "Biologic strategies for the therapy of intervertebral disc degeneration," Expert Opin. Biol. Ther., vol. 3, No. 8, pp. 1209-1214, Dec. 2003.

Masuda, K. et al., "Growth factors and the intervertebral disc," The Spine Journal, Elsevier, vol. 4, No. 6, pp. 330S-340S, Nov. 2004.

Roberts, S. et al., "Matrix Metalloproteinases and Aggrecanase: Their Role in Disorders of the Human Intervertebral Disc," SPINE, vol. 25, No. 23, pp. 3005-3013, 2000.

* cited by examiner

```
                          SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccttgaaggg atttccctcc                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggaacttccc taaagggagg                                                      20

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatctaggga tttccgggaa atgaagct                                             28

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agcttgagat agagct                                                          16

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcaagacc ttttcccaag aaatctat                                             28

<210> SEQ ID NO 6
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agcttgtgag tcagaagct                                              19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattcaccgg aagtattcga                                             20
```

METHODS AND COMPOSITIONS FOR TREATING, INHIBITING AND REVERSING DISORDERS OF THE INTERVERTEBRAL DISC

STATEMENT REGARDING FEDERALLY SPONSORED RESEARCH

This invention was made with United States Government support in the form of a grant from the National Institutes of Health, Grant No. P01-AR48152-01. The United States Government has certain rights in this invention.

FIELD OF INVENTION

The present invention relates to treating, inhibiting and reversing intervertebral disc disorders by blocking transcription factors including the transcription factors, NF-κB, E2F, GATA-3, STAT-1, STAT-3, STAT-6, Ets and AP-1. More particularly, the present invention relates to restoring intervertebral disc integrity by blocking transcription factor activity.

BACKGROUND OF THE INVENTION

Back pain is the second most common ailment complained about in doctors' offices after the common cold and is responsible for some 100 million lost days of work annually in the United States alone. A major proportion of these back injuries result from disorders of the intervertebral discs in the spine. Although the exact pathogenesis of many intervertebral disc disorders is unknown, disorders such as degenerative disc disease are generally mechanically induced and biologically mediated.

The IVD consists of an outer annulus fibrosus (AF), which is rich in collagens that account for its tensile strength, and an inner nucleus pulposus (NP), which contains large proteoglycans (PGs) that retain water for resisting compression loading. Biologically, disc cells in both the AF and NP maintain a balance between anabolism and catabolism, or steady state metabolism, of their extracellular matrices (ECMs), and are modulated by a variety of substances including cytokines, enzymes, their inhibitors and growth factors such as insulin like growth factor (IGF), transforming growth factor β (TGF-β), and bone morphogenetic proteins (BMPs). Various enzymes, such as matrix metalloproteinases (MMPs), and cytokines, mediate the catabolic process, or breakdown of the matrix. The degeneration of an IVD is thought to result from an imbalance between the anabolic and catabolic processes, or the loss of steady state metabolism, that are maintained in the normal disc.

In a normal IVD, the ECM of the NP is synthesized and maintained throughout adult life by relatively few cells. In the adult human, most NP cells are chondrocyte-like, whereas NP cells in the young have a significant number of large notochordal cells. It is not known if both NP cell types synthesize the large-molecular-weight hydrophilic PG, termed aggrecan, which constitutes the most abundant molecule in the tissue. These aggrecan molecules interact extracellularly with long linear strands of hyaluronan (HA), forming aggregates that become entangled in a fibrillar network made up principally of type II collagen. The swelling, fluid and ion-transport properties, as well as the intrinsic mechanical properties of the collagen-aggrecan solid matrix govern the deformational behavior of the NP. The collagen network gives the tissue tensile strength and hinders expansion of the viscoelastic, under-hydrated, aggrecan molecules that provide compressive stiffness and enable the tissue to undergo reversible deformation.

The AF contains a relatively homogeneous population of chondrocyte-like cells that synthesize a matrix richer in collagen and poorer in PG than cells from the NP, although the presence of different populations of cells and the zonal differences of matrix metabolism is suggested. Importantly, some of the AF cells synthesize PG and collagen molecules not normally found in significant amounts in cartilage. The progressive loss of the PG content of the IVD, with subsequent dehydration of the NP, has been implicated in the pathogenesis of IVD degeneration.

Unfortunately, current treatment of intervertebral disc disorders, including IVD degeneration, has been limited to only a few courses of action, the most common of these being spinal surgery. Even though in some cases spinal surgery achieves over 90% good to excellent results, the pathological IVD, with time, continues to undergo degeneration and significant disability may still result. Furthermore, although surgical techniques such as lumbar spinal fusion have a high success rate if performed on patients with deformities or documented instabilities such as spondylolisthesis and scoliosis, the outcome of surgical procedures for low back pain without radiculopathy is unpredictable.

In addition to often being unable to predict the outcome, there are a number of drawbacks to surgical procedures such as spinal fusion. First, the ability of the bone to heal or "fuse" varies; the average success rate of a lumbar spinal fusion is approximately 75%-80%. Unfortunately, the failure of fusion may be associated with continued symptoms. Second, a spinal fusion at one or more levels causes stiffness and decreased motion of the spine. Third, having a spinal fusion at one or more levels will cause more stress to be transferred to adjacent levels. Transferred stress may cause new problems to develop at other levels, leading to additional back surgery. For these reasons, numerous investigators are working on alternative treatments to spinal fusion including intradiscal electrothermal therapy (IDET), disc prostheses, and biological repair.

While some of the alternatives to spinal fusion show promise, there are still many disadvantages. For example, although IDET may relieve discogenic pain in patients, it does not restore structure or the biological matrices of the disc. As another example, the use of disc prostheses in disc replacement requires a surgical procedure and its associated potential surgical morbidities. In addition to the potential complications associated with undergoing surgery and general anesthesia, complications associated with artificial disc replacement may include breakage of the metal plate, dislocation of the implant, and infection. Like joint replacement surgery, artificial implants may fail over time due to wear of the materials and loosening of the implants.

What is needed is a non-invasive method that can result in the restoration of structure of the IVD. Currently, there are no non-invasive methods, such as treatment using pharmaceuticals that can accomplish these goals. Steroids are currently used to treat intervertebral disc disorders but steroids have many significant drawbacks in that they only control the symptoms of IVD degeneration and do nothing to stop, prevent, or reverse further injury.

Because of the drawbacks of steroid use, recent interest for the treatment of IVD disorders has focused on pharmaceuticals that can treat or prevent IVD disorders by targeting certain IVD biochemical mechanisms. The biochemistry of the IVD plays an important role in its mechanical properties. The NP is able to maintain its fluid pressure to balance the high external loads on the IVD because of the abundance of negatively charged PGs. This molecular meshwork of PGs entrapped in a collagen network endows the IVD with both compressive stiffness and tensile strength. One of the biological strategies for IVD repair is to enhance the synthesis of PGs and collagen, which may restore biomechanical function of the matrix.

In the IVD, the ECM content of PGs and the synthesis of PGs by chondrocytes embedded in the ECM decreases markedly with age and degeneration. Several cytokines [i.e. interleukin-1, (IL-1)] and proteinases [i.e., stromelysin and other MMPs] have been detected in degenerated or herniated IVDs. Interleukin-1α also stimulates the production of some of the MMPs, nitric oxide and prostaglandin E2 by normal IVD cells while inhibiting PG synthesis. Misregulation of these inflammatory cytokines and proteases likely contribute to IVD disorders such as IVD degradation. A strategy for biological treatment of IVD disorders such as intervertebral disc degeneration is to halt or counteract these cytokines by delivering inhibitors or other substances that block their enzymatic or catabolic activities. For example, IL-1 receptor antagonist (IL-1 Ra) has been investigated as a candidate to block IL-1 function in the IVD. Another strategy for biological treatment includes treating or preventing IVD disorders by preventing the expression of the genes that encode the proteins active in IVD disorders. One way to block the expression of these genes is to block the transcription factors that act upon them.

For example, the matrix metalloproteinase genes are generally controlled by several transcription factors including transcription factors that act on the PEA3 and AP-1 transcription factor sites. See Chakroborti et al. MOL CELL BIOCHEM 253: 269-285 (2003). One example of a transcription factor that plays a critical role in the regulation of many genes that control many of the biochemical factors active in IVD disorders such as the Matrix Metalloproteinases, is Nuclear Factor—kappa B (NF-κB), a complex group of heterodimeric and homodimeric transcription factors. Members of the NF-κB family include NF-κB1 (p50/p105), NF-κB2 (p52/p100), RelA (p65), RelB, and c-Rel. These molecules are trapped in the cytoplasm as an inactive complex by IκB, Dissociation of the transcription factor NF-κB from this complex has been reported to play a pivotal role in the regulation of inflammatory cytokine production, by inducing a coordinated transactivation of such genes as TNFα, IL-1, IL-6, IL-8, granulocyte-macrophage colony-stimulating factor (GMCSF), metalloproteinases and intercellular adhesion molecule 1 (ICAM-1). In rheumatoid arthritis (RA), the activation of NF-κB in synovium has been observed.

It has been hypothesized that blocking NF-κB family members may be able to reduce the degradation of articular cartilage tissue. The addition of NF-κB decoy oligonucleotides (ODN) by intraarticular injection in the bilateral hind ankle joints of collagen-induced arthritis (CIA) rats using the hemagglutinating virus of Japan (HVJ)-liposome method has shown a decrease in the severity of hind-pay swelling and a marked suppression of joint destruction. Unfortunately, rat articular ankle cartilage differs substantially from the fibrocartilage found in the human intervertebral disc. Inhibition of NF-κB has not been shown to prevent or treat fibrocartilage degradation in any species. Likewise, inhibition of NF-κB has not been shown to have biological effects on human primary fibrochondrocytes, specifically human primary fibrochondrocytes in vitro.

It has been hypothesized that blocking certain enzymes and cytokines believed to be active in IVD disorders at a transcriptional level may be used in the prevention or treatment of IVD disorders. Nevertheless, until the present invention there were no effective pharmaceuticals that acted using this principle.

SUMMARY OF THE INVENTION

One aspect of the present invention provides a method for treating IVD disorders by administering a transcription factor inhibitor to a pathological intervertebral disc. In certain embodiments, the transcription factor blocked by the transcription factor inhibitor may be NF-κB, E2F, GATA-3, STAT-1, STAT-3, STAT-6, Ets or AP-1. In this method, the pathological intervertebral disc may be in vivo or in vitro. In certain embodiments, treating IVD disorders includes preventing further pathology.

In another embodiment of the invention, methods are provided which prevent intervertebral disc disorders by blocking transcription factors in healthy intervertebral disc or healthy intervertebral disc tissue. The healthy intervertebral disc may comprise nucleus pulposus or annulus fibrosus tissue or cells.

Yet another aspect of the invention comprises a pharmaceutical composition, which comprises a transcription factor inhibitor, for treatment of intervertebral disc disorders. In this embodiment, the pharmaceutical composition may include a naked oligodeoxy-nucleotide decoy that blocks the ability of the transcription factor to act on the transcription factor responsive gene.

DETAILED DESCRIPTION OF PREFERRED EMBODIMENTS

Figure 1:
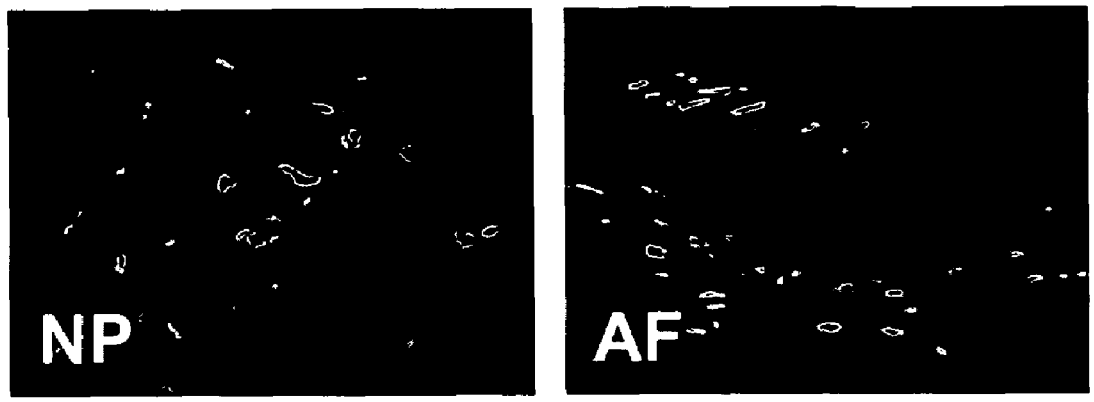
FIG. 1 shows cryosections of in vivo nucleus pulposus (NP) and annulus fibrosus (AF) cells 7 days following transfection with naked ODN demonstrating the distribution of FITC-labeled decoy ODN within the cells.

This invention is based on the use of methods of preventing, treating or repairing intervertebral disc disorders using one or more compounds that block the activity of transcription factors. These transcription factor inhibitors act on the transcription factors responsible for controlling the genes for the enzymes and cytokines involved in intervertebral disc disorders. This invention further relates to pharmaceutical compositions for treating IVD disorders, which comprise one or more transcription factor inhibitors. Generally, these transcription factor inhibitors may block the activity of transcription factors such as NF-κB, E2F, GATA-3, STAT-1, STAT-3, STAT-6, Ets and AP-1. In one embodiment, these compounds specifically block the activity of NF-κB.

Also described are methods of stimulating the synthesis of intervertebral disc cells and tissues using the methods and pharmaceutical compositions of the invention. Generally, the methods involve administering or contacting one or more transcription factor inhibitors to an intervertebral disc cell or tissue. The intervertebral disc cell or tissue may include fibrochondrocytes from the annulus fibrosus or nucleus pulposus. Commonly, these fibrochondrocytes can be isolated or contained within in vivo fibrocartilage. In typical embodiments, the fibrocartilage and fibrochondrocytes used with the methods of the invention will be mammalian, which can include placental, monotreme or marsupials. In some embodiments, the mammal is a canid, felid, murid, leporid, ursid, mustelid, ungulate, ovid, suid, equid, bovid, caprid, cervid, or a human or non-human primate. In specific embodiments, the fibrocartilage and fibrochondrocytes will be isolated or contained within an intervertebral disc of a human.

The present invention provides methods of treatment or reparation of direct or indirect fibrocartilage and IVD destruction by inhibiting transcription factor activity. As understood by the skilled artisan, inhibition of the transcription factor is accomplished by administering an effective amount of a transcription factor inhibitor to the cells or tissue of an intervertebral disc. The compositions and methods of the invention inhibit transcription factors active in controlling the genes involved in IVD disorders. Along with degenerative intervertebral discs, non-limiting examples of IVD disorders include low back pain, scoliosis, cervicodynia, hernia, and spinal canal stenosis (spinal stenosis).

In some embodiments, the compounds used to block the transcription factors will specifically act on transcription factors active in controlling the matrix metalloproteinase genes. For a review of examples of transcription factors active in the control of matrix metalloproteinase genes, please see Vincenti and Brinckerhoff, ARTHRITIS RES 4:157-164 (2002) and Chakroborti et al. MOL CELL BIOCHEM 253: 269-285 (2003), both of which are hereby incorporated by reference. In other embodiments, the compounds used to block the transcription factors will specifically act on transcription factors active in controlling the interleukin genes. In yet further embodiments, the compounds may specifically act on transcription factors active in controlling both matrix metalloproteinase genes and interleukin genes. As understood by the skilled artisan, the transcription factor inhibitors may be used to block any gene found to be involved in an intervertebral disc disorder.

Effective amounts of one or more transcription factor inhibitors will be administered to the intervertebral disc. In many embodiments, the intervertebral disc will be in vivo. When the intervertebral disc is in vivo, the transcription factor inhibitory compound can be administered through any method that will deliver an effective amount of the transcription factor inhibitory compound. The transcription factor inhibitory compound can be used to treat an intervertebral disc disorder, such as a herniated disc, or the transcription factor inhibitory compound can be administered prophylactically to prevent intervertebral disc disorders. Generally, in many intervertebral disc disorders, the extracellular matrix displays breakdown of components as compared to normal tissue. This breakdown can be determined by measuring the presence of enzymes known to be active in cleaving members of the extracellular matrix. The breakdown can also be determined by measuring the height of the intervertebral disc.

Figure 5:
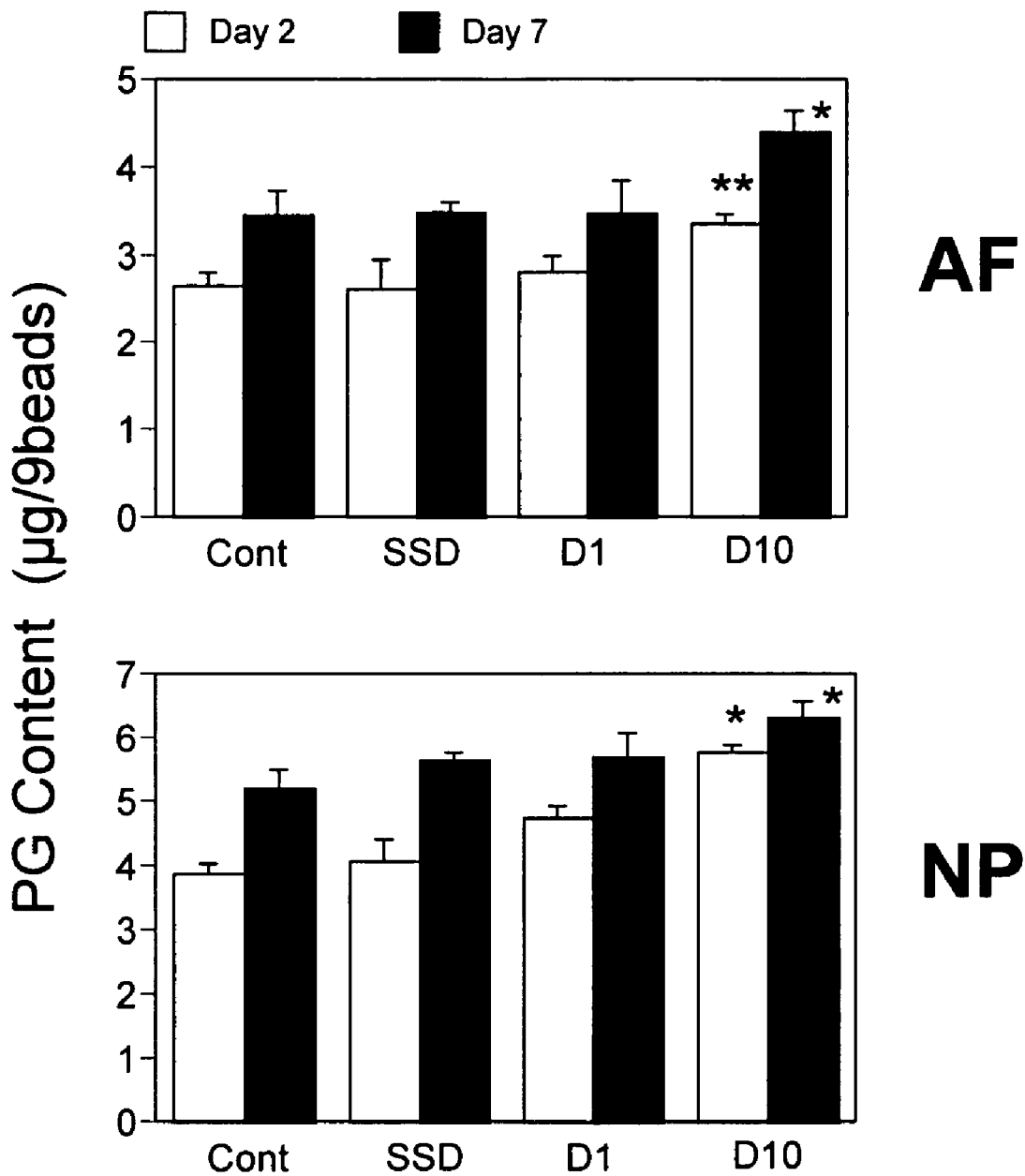
FIG. 5 demonstrates that treatment with ODN decoy significantly stimulates the accumulation of proteoglycan (PG) in human cultured AF and NP cells.

Surprisingly and unexpectedly, it was found that in some embodiments, blocking transcription factors in the intervertebral disc resulted in a reversal of previous damage. Generally, it is believed as a non-limiting theory that reversal exists when the growth of extracellular matrix is stimulated. As demonstrated by FIG. 2, disc height in an annular puncture model increased as compared to non-treated discs following a double-injection of a transcription factor inhibitor. Similarly, as shown in FIG. 5, AF and NP cells treated with a transcription factor inhibitor have an enhanced capacity to form extracellular matrix. Taken together, this suggests that transcription factor inhibitors and methods of the invention reverse previous intervertebral disc damage. This is the first instance of a transcription factor inhibitor resulting in reversal of the damage found in pathological intervertebral disc.

In certain methods of the invention, the in vivo intervertebral disc will not have suffered an injury or become arthopathic before the transcription factor inhibitor is administered. In other embodiments, the present invention provides a method for treating an intervertebral disc disorder, such intervertebral disc degeneration. The pathology in the intervertebral disc can exist in the annulus fibrosus, the nucleus pulposus, or both. A non-limiting example of a pathological intervertebral disc includes a disc undergoing degeneration, which can result in disc herniation. Degeneration can also result in back pain.

In some embodiments, before a transcription factor inhibitor is added to an intervertebral disc, the level of intervertebral disc pathology will be measured. Measurement of the pathology of disorders of the intervertebral disc can be accomplished in a variety of ways. In asymptomatic or symptomatic patients, this can include MRI or CT myelography. Intervertebral disc disorders can also be diagnosed by using a plain radiographs, CT scans, and discography, a method where spinal needles are placed into the cervical intervertebral discs to identify symptomatic discs.

Disorders of the intervertebral disc can also be measured biochemically by changes in the normal proportion and types of proteoglycan and collagen or by an increase in the levels of matrix degrading enzymes. Furthermore, because increased cytokine expression is a likely contributor to certain intervertebral disc disorders, the present invention encompasses measurement of cytokines as a means to ascertain intervertebral disc disorders. Other biochemical measurements to detect intervertebral disc disorders can include, but are not limited to, sensing a reduction in the total number of cells or an increase in the number of cells undergoing apoptosis. As nerves and blood vessels grow into diseased intervertebral discs, measuring the change in angiogenesis factors, vascularization or innervation may be also used as markers of intervertebral disc disorders.

Following administration of the transcription factor inhibitor, to determine the efficacy of the treatment, the present methods encompass determining or measuring the level of intervertebral disorder. In some embodiments, the methods may involve determining or measuring the level of intervertebral disorder before treatment in order to establish the amount of transcription factor inhibitor needed sufficiently to treat a pathological intervertebral disc. In these embodiments of the invention, the level of fibrocartilage degrading factors or their precursors, e.g. pro-enzymes, mRNA, etc., can be measured to ascertain the amount of fibrocartilage degradation. Generally, a fibrocartilage-degrading factor encompasses any compound that, when present, will lead to the degradation of fibrocartilage tissue in an intervertebral disc. The fibrocartilage-degrading factor can act directly on fibrochondrocytes or fibrocartilage tissue to cause degradation, affect a compound that directly degrades fibrocartilage tissue, or affect a modulator of a compound that degrades fibrocartilage tissue. Fibrocartilage degrading factors include enzymes that directly degrade the cartilage matrix as well as other chemicals that stimulate cartilage degradation, including cytokines such as IL-1. IL-1 appears indirectly to cause fibrocartilage degradation by at least upregulating matrix metalloproteinase activity. Non-limiting examples of methods of measuring fibrocartilage-degrading factors include measuring nitric oxide (NO) production, proteinase detection, or both.

Proteinases, which occupy a specific group of fibrocartilage degrading factors, can be detected in normal and pathological intervertebral discs. These proteinases include, but are not limited to, matrix metalloproteinases (MMPs) and members of the ADAMTS family. In the invention, fibrocartilage-degrading factors including proteinases can be detected by any method known in the art. These methods include Western Blot analysis, immunohistochemistry, detection of RNA transcripts, and zymography. The fibrocartilage or fibrochondrocytes from the intervertebral disc can be treated with a fibrochondroprotective agent before measurement of the fibrocartilage degrading factors. Detection can also be conducted before contact, after contact, or both of a fibrocartilage-degrading factor. In one embodiment, the fibrocartilage degrading factors will be natural factors. Another embodiment of the invention contemplates the use of synthetic fibrocartilage degrading factors. Specifically, in one embodiment, the cartilage-degrading factor can be IL-1. In another embodiment, the cartilage-degrading factor can be a proteinase such as an ADAMTS family member.

For the embodiments utilizing in vitro fibrocartilage and fibrochondrocytes, the fibrocartilage and fibrochondrocytes can be isolated directly from pre-existing intervertebral disc tissue. Fibrochondrocytes used for preparation of in vitro cell culture can be isolated by any suitable method known in the art. Various starting materials and methods for cell isolation are known. See generally, Freshney, Culture of Animal Cells: A Manual of Basic Techniques, 2d ed., A. R. Liss Inc., New York, pp 137-168, 1987; Klagsburn, "Large Scale Preparation of Chondrocytes," METHODS ENZYMOL 58:560-564, 1979. In vitro fibrocartilage and fibrochondrocytes should retain their fibrocartilage phenotype and produce a cell-associated matrix having collagen and proteoglycan contents characteristic of the fibrocartilage source from which they were isolated. In some embodiments, the chondrocytes will be cultured in alginate beads. In other embodiments, the fibrocartilage cells, specifically including nucleus pulposus and annulus fibrosus cells, will be cultured until they form a cartilage tissue, such as that disclosed in U.S. Pat. Nos. 6,451,060 and 6,197,061. Following the formation of cartilage tissue, the cartilage tissue may be used to test the effects of different types of transcription factor inhibitors in vitro.

Because the fibrochondrocytes from the intervertebral disc may be found either in vivo or in vitro, both the type of transcription factor inhibitor and the method of contacting the transcription factor inhibitor with the fibrochondrocytes can vary. For example, when the fibrochondrocyte is in vitro, a transcription factor inhibitory compound, such as a naked decoy oligodeoxy-nucleotide can be added or included in the medium in which the fibrochondrocyte is being maintained or cultured.

As used herein, a "transcription factor inhibitor" or a "transcription factor inhibitory compound" is any compound that inhibits the ability of a transcription factor to activate or suppress responsive genes involved in intervertebral disc disorders. In some embodiments, the transcription factor inhibitors will act on transcription factors that activate genes. In other embodiments, the transcription factor inhibitors will act on transcription factors that inhibit genes. One of skill in the art understands that a single transcription factor inhibitor may act on both transcription factors that activate and transcription factors that inhibit different genes. The skilled artisan also understands that the transcription factor inhibitor may act either directly on the transcription factor that acts directly on the responsive gene or on any member of the transcription factor pathway that leads to transcriptional activity or inhibition by the transcription factor. For example, U.S. Patent Appl. No. 20040171823 discloses polynucleotides and polypeptides active in the NF-κB pathway. In certain embodiments, the polynucleotides and polypeptides of U.S. Patent Application No. 20040171823 may be blocked using the methods of the present invention.

Examples of transcription factor inhibitor compounds include anti-oxidants, proteasome inhibitors, peptides, small molecules, decoy oligonucleotides and dominant-negative or constitutively active polypeptides. Transcription factor inhibitors may also include decoys, antisense molecules, ribozymes, aptamers, siRNA, antibodies and antagonists. In certain embodiments, the transcription factor inhibitors will inhibit the transcription factor before translation of the transcription factor RNA. In other embodiments, the transcription factor inhibitors will inhibit the transcription factor following translation of the transcription factor RNA. Specific examples of non-nucleotide based transcription factor inhibitors include glutathione, cyclosporine A, estrogen, and leptomycin B.

It is within the bounds of routine experimentation and therefore, within the scope of the instant invention for the skilled artisan to determine an appropriate transcription factor inhibitor for a particular use. For example, as is well demonstrated in the art, in the cases where a nucleotide transcription factor such as a decoy or a SiRNA is chosen, the particular transcription factor inhibitor will be selected based on nucleotide sequence. For example, when the transcription factor inhibitor is a decoy, the sequence of the decoy will be selected to match closely the sequence of the responsive gene where the transcription factor normally binds. As another non-limiting example, when the transcription factor inhibitor is an antibody, the antibody will be selected based on its ability to interact with the transcription factor. Thus, using the knowledge currently known in the art, the skilled artisan can determine the appropriate transcription factor inhibitor based on the transcription factor that is to be inhibited and the desired method of inhibition. In some embodiments, the transcription factor inhibitors will be natural molecules. In other embodiments, the transcription factor inhibitors will be synthetically designed molecules. The transcription factor inhibitors may act as general inhibitors of induction of members of the transcription factor family or as inhibitors of specific pathways of induction. The skilled artisan understands that the transcription factor inhibitors specifically disclosed are meant to be illustrative only and many other types of transcription factor inhibitors may be used with the methods of the invention. In some embodiments, certain inhibitors may be used to prevent or treat fibrocartilage degradation in vitro but will not be appropriate for preventing or treating fibrocartilage degradation in vivo. For an in-depth discussion of examples of the types of inhibitors that may be used in the invention, see Epinat & Gilmore, ONCOGENE 18: 6896-6909 (1999) and Barnes, INT J BIOL 29(6): 867 (1997), both of which are hereby incorporated by reference. The advantages and disadvantages of many types of transcription factor inhibitors used as therapeutic agents are known in the art.

In one embodiment of the invention, decoy oligodeoxy-nucleotides (ODN) which are described in Tomita et al., Rheumatology 39: 749-757 (2000), U.S. Pat. No. 6,262,033, U.S. patent application Ser. No. 10/366,718 and PCT Patent Appl. No.: PCT/JP02/00990, all of which are incorporated by reference, will be used to inhibit transcription factors. The term "decoy" refers to a compound which binds to a site on a chromosome, which a transcription factor binds to, or a site on a chromosome, which another transcription regulatory factor for a gene controlled by a transcription factor such as NF-κB (hereinafter referred to as a target binding site) binds to, and antagonizes the binding of NF-κB, Ets, or other transcriptional factors to these target binding sites.

Generally, when a decoy is present within a nucleus of a cell, the decoy conflicts with a transcription regulatory factor competing for a target binding site, for the transcription regulatory factor. As a result, a biological function, which would be generated by binding of the transcription regulatory factor to the target binding site, is inhibited. The decoy contains at least one nucleic acid sequence capable of binding to a target binding sequence. A decoy can be used for preparation of a pharmaceutical composition according to the present invention as long as the decoy can bind to a target binding sequence. The transcription factor inhibition by the decoy can occur at both an in vitro and an in vivo level. In some embodiments, decoy oligodeoxy-nucleotides will be administered to the fibrocartilage before any appreciable cell death can be measured. In individual embodiments, blocking the transcription factor NF-κB will be accomplished using decoy oligodeoxy-nucleotides with the following specific sequences 5'-CCTTGAAGGGATTTCCCTCC-3' (SEQ ID NO.: 1) and 3'-GGAACTTCCCTAAAGGGAGG-5' (SEQ ID NO.: 2). Decoys for other transcription factors may include, but are not limited to, the following sequences 5'-GATCTAGGGATTTCCGGGAAATGAAGCT-3' (SEQ ID NO: 3) (STAT-1 decoy); 5'-AGCTTGAGATAGAGCT-3' (SEQ ID NO.: 4) (GATA-3 decoy); 5'-GATCAAGAC-CTTTFCCCAAGAAATCTAT-3' (SEQ ID NO.: 5) (STAT-6 decoy); 5'-AGCTTGTGAGTCAGAAGCT-3' (SEQ ID NO.: 6) (AP-1 decoy); and 5'-AATFCACCGGAAGTATFCGA-3' (SEQ ID NO.: 7) (Ets decoy). When decoy oligonucleotides are used, decoy oligonucleotides can be made using standard nucleotide synthesis or cloning methods known in the art. These oligonucleotides may be DNA or RNA and may contain modified nucleotides and/or pseudonucleotides. Furthermore, oligonucleotides when used with the methods of the present invention maybe single-stranded or double stranded and linear or cyclic. In some embodiments, the oligonucleotides will be double-stranded.

In the embodiments where decoy oligodeoxy-nucleotides are used to block transcription factors, the decoy ODNs may be introduced into the applicable cells and tissues using a variety of methods. In certain methods, the cells or tissue of interest may be transfected using "naked" oligodeoxy-nucleotides. As used in this context, "naked" oligodeoxy-nucleotides describe ODNs that are introduced by simply administering the ODN without transfection aids, such as liposomes, which are commonly used in gene therapy. Although it is known in the art to transfect gene sequences using adenovirus-mediated transfer and to transfer naked gene sequences that incorporate into the DNA of the cells of the intervertebral disc, the present invention differs in that "naked" decoy is transfected into the cells but acts as a transcription factor inhibitor for a period of time without integrating into the genome of the intervertebral disc cell. The methods known in the art are described in Zhao et al. Chin Med J 115(3): 409-412 (2002) and U.S. patent application Ser. No. 09/199,978, both of which are hereby incorporated by reference.

It was surprising and unexpected that transfection of the naked decoy ODN to both in vivo and in vitro fibrochondrocytes would result in sustained transcription factor inhibitory action. Previous reports have suggested that naked oligonucleotides cannot be retained in cells. As demonstrated by FIG. 1, decoy ODN can be visualized in NP and AF cells in vivo 7 days post transfection. Decoy ODN could also be visualized in the cytoplasm and nuclei of in vitro NP and AF cells two days post-transfection. Although others in the art have suggested that naked transfection of decoy ODN does not result in appreciable retention, the transfection of naked decoy ODN may be viable in the methods of the current invention because fibrocartilage from the intervertebral disc is a specialized form of cartilage that differs from the tissue previously used, such as articular cartilage.

The skilled artisan understands the many differences between fibrocartilage from an intervertebral disc and articular cartilage. For example, antenatal differentiation of the fibrocartilage intervertebral disc is different from that of the articular cartilage in a synovial joint. The intervertebral discs are never directly affected by synovial disorders such as rheumatoid arthritis. In fact, the human fibrocartilage intervertebral disc has a complex, specific developmental history as compared to other joints in the body. This is because of the presence of the notochord that has no equivalent in the synovial joints. In human adults, the vascular supply differs considerably between a synovial joint, in which it is well developed, and the adult intervertebral disc, which is the largest avascular structure of the human body. Scanning electron microscopy of the intervertebral disc has shown that the nucleus pulposus is composed of a three-dimensional lattice gel, supported by a loose network of fine fibrils enmeshing fibroblastic cells, and intercellular material, with a gradual transition from the fibrous network to the lamellae of the annulus. In contrast, a true synovial joint contains numerous synoviocytes.

Pharmaceutical compositions of transcription factor inhibitory compounds such as decoy ODN, can be prepared by mixing one or more transcription factor inhibitory compounds with pharmaceutically acceptable carriers, excipients, binders, diluents or the like, to therapeutically treat, reverse or ameliorate a variety of intervertebral disc disorders. A therapeutically effective dose refers to that amount of one or more transcription factor inhibitory compounds sufficient to result in amelioration of symptoms of the intervertebral disc disorder. An effective dose can also refer to the amount of one or more transcription factor inhibitor compounds sufficient to result in prevention of the intervertebral disc disorder. In some embodiments, the effective dose will only partially prevent the intervertebral disc disorder. In these cases, the disorder of the intervertebral disc, although it may still exist, will be less than the expected intervertebral disc disorder if no treatment had been given.

The pharmaceutical compositions can be manufactured by methods well known in the art such as conventional granulating, mixing, dissolving, encapsulating, lyophilizing, emulsifying or levigating processes, among others. In certain embodiments, the transcription factor inhibitory compounds can be administered in a local rather than a systemic fashion, such as injection as a sustained release formulation. In some embodiments, an effective amount of the transcription factor inhibitory compounds can be administered in any satisfactory physiological buffer such as a phosphate buffer solution (PBS) or in a 5% lactose solution to the pathological intervertebral disc. The dosage forms disclosed in the instant specification are given by way of example and should not be construed as limiting the instant invention.

The formulations of the transcription factor inhibitory compounds can be designed for to be short acting, fast releasing, long acting, and sustained-releasing as described below. Thus, the pharmaceutical formulations can also be formulated for controlled release or for slow release, such as being contained within a biodegradable matrix or carrier.

The transcription factor inhibitor in the instant compositions can also exist in micelles or liposomes, or some other encapsulated form, or can be administered in an extended release form to provide a prolonged storage and/or delivery effect. Therefore, the pharmaceutical formulations can be compressed into pellets or cylinders and implanted as stints. Such implants can employ known inert materials such as silicones and biodegradable polymers.

A therapeutically effective dose of a transcription factor inhibitor can vary depending upon the route of administration and dosage form. The exact dose is chosen by a physician in view of the condition of a patient to be treated. Doses and administration are adjusted to provide a sufficient level of the active portion, or to maintain a desired effect. Specific dosages can be adjusted depending on conditions of disease, the age, body weight, general health conditions, sex, and diet of the subject, dose intervals, administration routes, excretion rate, and combinations of drugs. A sustained action pharmaceutical composition may be administered repeatedly within a certain interval such as every 3 to 4 days, every week, or once per two weeks (bi-monthly), depending on the half-life and clearance rate of a specific preparation. Guidance for specific doses and delivery methods are provided in publications known in the art. Any of the above dosage forms containing effective amounts are well within the bounds of routine experimentation and therefore, well within the scope of the instant invention. In some embodiments, an effective amount of transcription factor inhibitor will be less than or equal to 500 micrograms. In other embodiments, an effective amount of transcription factor inhibitor will be less than or equal to 200 micrograms.

In one embodiment, the transcription factor inhibitory compound or compounds is a formulation that exhibits a high therapeutic index. The therapeutic index is the dose ratio between toxic and therapeutic effects that can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals.

In some embodiments, the transcription factor inhibitory compound or compounds are administered directly to the in vivo fibrocartilage of interest. For example, the transcription factor inhibitory compound can be administered directly into the intervertebral disc, such as by injecting the transcription factor inhibitory compound into the annulus fibrosus, nucleus pulposus, or both. Due to the avascular nature of intervertebral discs, direct injection into the intervertebral disc has the potential of providing faster acting and lower dose treatment than administering the transcription factor inhibitory compound through a different route.

The present invention also provides kits for carrying out the methods described herein. The present kits can also include one or more reagents, buffers, media, proteins, analytes, labels, cells, computer programs for analyzing results, and/or disposable lab equipment, such as culture dishes or multi-well plates, in order to readily facilitate implementation of the present methods. Solid supports can include beads, culture dishes, multi-well plates and the like. Examples of preferred kit components can be found in the description above and in the following examples.

This present methods are further illustrated by the following non-limiting examples.

EXAMPLES

In all examples, phosphorothioate double-stranded decoy ODN having the sequences: 5'-CCTTGAAGGGATTTC-CCTCC-3' (SEQ ID NO.: 1); 3'-GGAACTTCCCTAAAGG-GAGG-5' (SEQ ID NO.: 2), designed to be recognized by the NF-κB binding site were used.

Example 1

Reversal of In Vivo Intervertebral Disc Degeneration Following Treatment with a NF-κB Inhibitor In this example, an intra-discal injection of naked NF-κB decoy was effective in partially restoring the disc height in a rabbit annular puncture model. Under general anesthesia twenty-four New Zealand White rabbits (3 kg), used with IACUC approval, received an annulus puncture in two non-contiguous lumbar IVDs (L2/3 and L4/5) with an 18G needle to a 5 mm depth to induce disc degeneration. Discs at L3/4 served as non-punctured controls. The rabbits were equally divided into three groups, which included a punctured control, a single-injection and a double-injection group. For the single-injection group, at the initial puncture, 1 µg or 10 µg of NF-κB ODN in 10 µl vehicle was injected using a 28 G needle at either the L2/3 or L4/5 disc. For the double-injection group, four weeks after the initial puncture and injection of decoy, the same dose of NF-κB ODN decoy was injected into the punctured discs. Lateral X-rays of the lumbar spine were taken every two weeks to measure IVD height. Eight weeks after the first injection, lumbar spines were harvested and sagittal MRI images were taken.

The IVD height was measured with a custom program using MathLab software and the percent DHI (% DHI=postoperative DHI/preoperative DHI×100) was calculated. Sagittal MRI of the lumbar spine at L2/3, L3/4 and L4/5 were assessed for MRI grade of disc degeneration using the MRI grading scale (0-3) as previously described. Differences among the groups were assessed for statistical significance by repeated ANOVA and the Fisher's PLSD post hoc test. The Friedman test and Mann-Whitney U-test were applied for the MRI grading.

Figure 2:
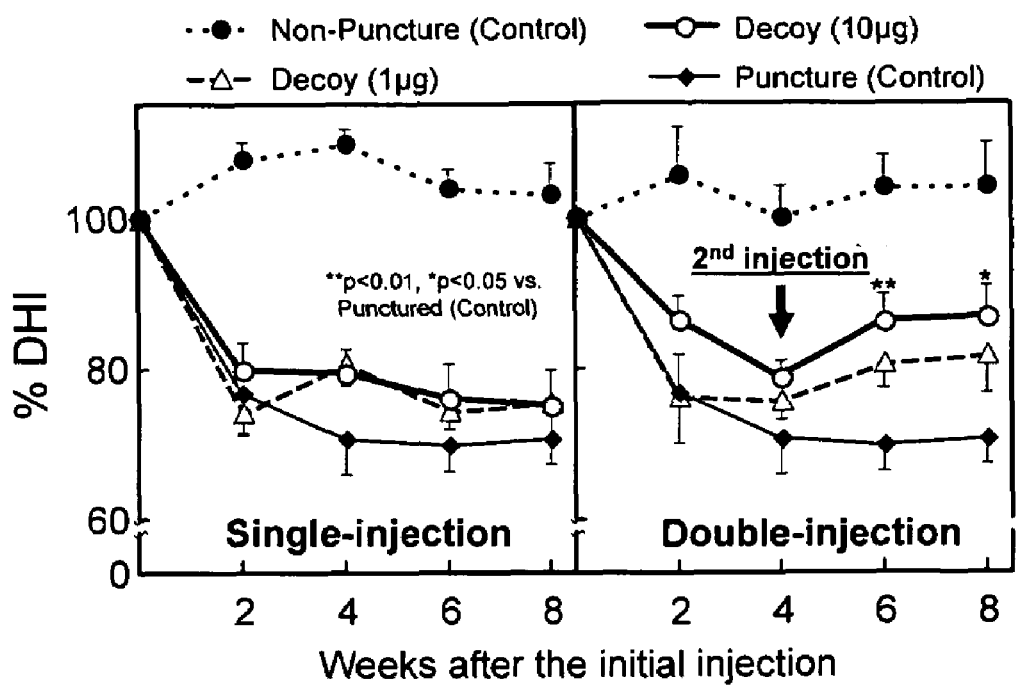
FIG. 2 is a graph demonstrating changes in % in vivo intervertebral disc height (DHI) (% DHI=postoperative DHI/preoperative DHI×100) in a rabbit IVD when either not punctured (non-puncture control), punctured but not treated (puncture control), treated with 1 μg decoy, or treated with 10 μg decoy.

As demonstrated by FIG. 2, the punctured group showed significant disc narrowing in the punctured discs two weeks after the puncture, which was maintained up to eight weeks (pre-op vs. 2W, 4W, 6W, 8W, all p<0.01). In the single-injection group, there were no significant differences in the % DHI among the discs injected with 1 µg or 10 µg of decoy ODN and the punctured control discs at any time point. Four weeks after the initial surgery, in the double-injected animals, the DHI of the 1 µg and 10 µg decoy ODN groups showed no significant differences from the punctured group, as was also seen in the single injection group (DHI at 4W, punctured control: 71.4±5.2%; 1 µg: 75.8±2.4%; 10 µg: 78.7±2.4%). However, after the second injection of decoy ODN at four weeks, the disc height began to recover and at six and eight weeks in the discs injected with either 1 µg or 10 µg of decoy ODN, the disc height trended towards the non-punctured control level. The recovery was significant in the 10 µg group (1 µg, 6W: 80.7±3.2%, p=0.07; 8W: 81.8±5.0%, p=0.12; 10 µg, 6W: 86.1±3.8%, p<0.01; 8W: 86.7±4.3%, p<0.05 vs. punctured control).

MRI grading scores showed significant differences between the punctured group and the decoy-injected group (Control [puncture]: 2.1±0.6; single-injection [1 μg]: 1.4±0.7, p<0.01; single-injection [10 μg]: 1.7±0.7, p<0.05; double-injection (1 μg): 1.8±0.7, p=0.21; double-injection (10 μg): 1.7±0.6, p<0.05, vs. control [puncture]).

To examine the distribution of decoy ODN in vivo, FITC-labeled decoy ODN (10 μg) was injected into rabbit discs (L2/3 and L4/5) after annulus puncture as described above. On day-7 after the injection, under deep anesthesia, the rabbits were fixed, using a perfusion fixation technique. The animals were sacrificed and the IVDs were removed. Cryosections (8 μm) were cut, and the samples were imaged using confocal microscopy. FIG. 1 demonstrates that on day-7 after injection, FITC-labeled decoy ODN was detected in both nucleus pulposus (NP) and annulus fibrosus (AF) tissues. Fluorescent intensity was confirmed in the nuclei and in the cytoplasm of the NP and AF cells.

Example 2

Decreased Response of In Vitro Intervertebral Disc Cells to IL-1 Following Treatment with a NF-κB Inhibitor This example illustrates the use of the methods of the invention to demonstrate that a NF-κB inhibitor when added to intervertebral disc cells significantly reduces the response of the cells to IL-1, a catabolic mediator as measured by the production of MMPs, TIMP-1, IL-6 and NO.

NP and AF cells from 65-70 yrs old donors were isolated and cultured in alginate beads at $4 \times 10^6$ cells/ml in complete media (DMEM/10% FBS/gentamicin/25 μg/ml ascorbic acid), which was changed daily. After five days of pre-culture in complete medium, the beads were cultured in serum-free medium without antibiotics for 24 hrs. The cells were then transfected with naked oligonucleotides comprising a scrambled decoy (SCD) 0.5 μM, a single stranded decoy (SSD) 1 μM, and decoy ODNs (0.5 μM) for four hours. Cells where no oligonucleotide was transfected were used as a control. Following transfection, FITC-labeled decoy ODN was used to determine the transfection efficiency. After transfection, the cells in the alginate beads were treated with or without IL-1β (5 ηg/ml) and incubated for 48 hrs.

Figure 4:
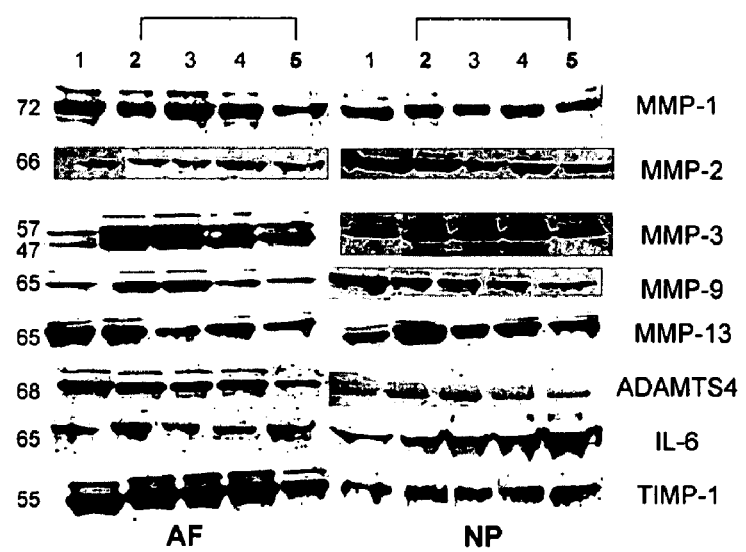
FIG. 4 shows a Western Blot that demonstrates the down-regulation of MMP expression following treatment with naked ODN. The lanes in the figure correspond to Lane 1: control, Lane 2: treatment with IL-1β; Lane 3: treatment with scrambled decoy and IL-1β; Lane 4: treatment with single stranded decoy and IL-1β; and Lane 5: treatment with decoy and IL-1β.

At the end of the incubation period, the media of the different treatments were collected for Western Blot and NO production analyses. For Western Blot analysis, shown in FIG. 4, the following antibodies were used: anti-MMP-1, anti-ADAMTS4 (Santa Cruz Biotechnology), anti-MMP-2 and -MMP-3 (Oncogene), anti-MMP-9 and -MMP-13, anti-TIMP-1, anti-IL-6. To measure the production of Nitric Oxide, a Nitric Oxide Assay Kit from R&D Systems was used. Statistical analysis was run using one-way ANOVA and Fisher's PLSD post hoc test.

Figure 3:
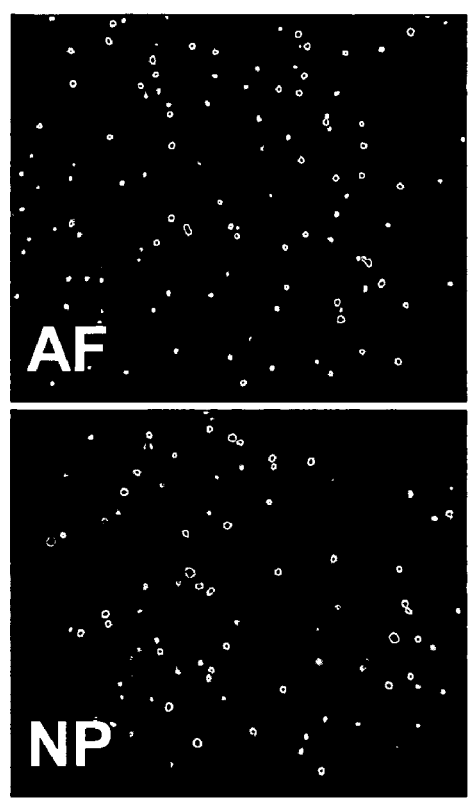
FIG. 3 shows in vitro nucleus pulposus (NP) and annulus fibrosus (AF) cells following transfection with naked ODN demonstrating the distribution of FITC-labeled decoy ODN within the cells.

To measure the transfection efficiency, the presence of FITC-decoy ODN in the cytoplasm and nuclei was confirmed in NP and AF cells with confocal microscopy (transfection efficiency≈80%) as demonstrated by FIG. 3. Without transfection of the ODN decoy, the addition of IL-1β to the media significantly increased MMP-1, -2, -3, -9, -13, ADAMTS4 and IL-6 protein levels, and significantly decreased TIMP-1 protein levels in the media of both AF and NP cells. As shown by the Western Blot of FIG. 4, transfection with decoy for four hours significantly decreased the protein levels of MMPs enhanced by IL-1 in both cell types (AF: MMP-1: 62%; MMP-2: 38%; MMP-3: 96%; MMP-9: 97%; MMP-13: 46%; ADAMTS4: 47%, NP: MMP-1: 31%; MMP-2: 54%; MMP-3: 35%; MMP-9: 43%; MMP-13: 24%; ADAMTS4: 42%) whereas significant increases in TIMP-1 levels were seen in NP cells. The addition of IL-1β also stimulated NO production by NP and AF cells about three-fold. The addition of IL-1β to cells transfected with decoy ODNs (0.5 μM) resulted in a marked reduction of the NO levels in the media, by 50% in AF cells and 66% in NP cells.

Example 3

Increase In Proteoglycan Content of Cultured AF and NP Cells Following Treatment with NF-κB Inhibitor This example illustrates the use of the methods of the invention to demonstrate that a NF-κB inhibitor when added to intervertebral disc cells significantly increases the proteoglycan content of AF and NP cells during culture.

NP and AF cells were isolated and pre-cultured in alginate beads in DMEM/10% FBS media for 14 days. After the pre-culture, the cells were either left untreated (Cont), treated with a single stranded NF-κB oligonucleotide (SSD) 2 μM for six hours, or treated with either 1 μM (D1) or 10 μM (D10) of a double stranded NF-κB decoy oligonucleotide for six hours. Following each treatment, the cells were further cultured for two or seven days. At the end of the culture, the alginate beads containing the NP and AF cells were digested with papain and the proteoglycan content of the cultured cells was measured by the dimethylmethylene blue dye binding method.

As demonstrated by FIG. 5, administration of 10 μM of double stranded NF-κB decoy was the only treatment capable of significantly increasing the amount of proteoglycan in cultured AF and NP cells (** p<0.01, * p<0.05). This increase in proteoglycan content supports that the disc height recovery in the in vivo studies must be more than inhibition of degradation. The recovery of disc height and the increase in the amount of proteoglycan demonstrate an enhancement of the capacity of the NP and AF cells to form matrix following treatment with NF-κB double stranded decoy.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods. As used herein a means "one" or "one or more."

As will be understood by one skilled in the art, for all purposes, particularly in terms of providing a written description, all ranges disclosed herein also encompass all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than," and the like include the number recited and refer to ranges that can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references disclosed herein are specifically incorporated by reference thereto.

While preferred embodiments have been illustrated and described, it should be understood that changes and modifications can be made therein in accordance with ordinary skill in the art without departing from the invention in its broader aspects as defined in the following claims.

What is claimed is:

1. A method for the treatment of intervertebral disc degeneration, comprising:
    administration of a NF-κB inhibitor into an intervertebral disc wherein administration of the NF-κB inhibitor treats an intervertebral disc degeneration, and wherein the NF-κB inhibitor is selected from the group consisting of: a decoy oligonucleotide capable of binding to the DNA binding site of NF-κB, an antisense NF-κB nucleic acid, and a NF-κB siRNA, and further wherein the NF-κB inhibitor acts directly on NF-κB, or directly on NF-κB mRNA.

2. A method for the treatment of intervertebral disc degeneration, comprising:
    administration of a NF-κB inhibitor into an intervertebral disc, wherein administration of the NF-κB inhibitor treats an intervertebral disc degeneration, and wherein the NF-κB inhibitor is a NF-κB decoy having the sequence of SEQ ID NO.: 1.

3. The method of claim 1, wherein the intervertebral disc disorder is diagnosed by discography.

4. The method of claim 1, wherein the NF-κB inhibitor is administered repeatedly with a certain interval.

5. The method of claim 4 wherein the certain interval is bi-monthly.

6. The method of claim 1, wherein an effective dose of the NF-κB inhibitor is less than or equal to 500 micrograms.

7. The method of claim 1, wherein an effective dose of the NF-κB inhibitor is less than or equal to 200 micrograms.

8. The method of claim 1, wherein the NF-κB inhibitor is administered in physiological buffer.

9. The method of claim 8 wherein the physiological buffer is a phosphate buffer solution or a 5% lactose solution.

* * * * *

UNITED STATES PATENT AND TRADEMARK OFFICE
CERTIFICATE OF CORRECTION

| | | |
|---|---|---|
| PATENT NO. | : 7,585,848 B2 | Page 1 of 1 |
| APPLICATION NO. | : 11/033466 | |
| DATED | : September 8, 2009 | |
| INVENTOR(S) | : Masuda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 535 days.

Signed and Sealed this

Twenty-eighth Day of September, 2010

David J. Kappos
*Director of the United States Patent and Trademark Office*